(12) United States Patent
Watson et al.

(10) Patent No.: US 8,642,164 B2
(45) Date of Patent: Feb. 4, 2014

(54) COMPOSITE SUBSTRATES WITH PREDETERMINED POROSITIES

(75) Inventors: Charles R. Watson, Windsor, CT (US); John H. Vontell, Manchester, CT (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 13/233,627

(22) Filed: Sep. 15, 2011

(65) Prior Publication Data

US 2013/0071603 A1 Mar. 21, 2013

(51) Int. Cl.
- *B32B 7/02* (2006.01)
- *B32B 3/26* (2006.01)
- *G01D 18/00* (2006.01)
- *G01N 3/62* (2006.01)
- *G01S 7/497* (2006.01)
- *G01C 25/00* (2006.01)

(52) U.S. Cl.
USPC ........... 428/212; 428/304.4; 73/1.01; 73/1.78

(58) Field of Classification Search
None
See application file for complete search history.

(56) References Cited

U.S. PATENT DOCUMENTS

| | | | |
|---|---|---|---|
| 4,286,455 A * | 9/1981 | Ophir et al. ..................... | 73/1.83 |
| 4,414,142 A | 11/1983 | Vogel et al. | |
| 5,127,268 A | 7/1992 | Kline | |
| 5,304,338 A | 4/1994 | Hertel et al. | |
| 5,344,700 A * | 9/1994 | McGath et al. ............ | 428/304.4 |
| 5,374,122 A * | 12/1994 | Devitt et al. ..................... | 374/45 |
| 5,449,273 A | 9/1995 | Hertel et al. | |
| 6,334,617 B1 | 1/2002 | Putnam et al. | |
| 7,434,468 B2 | 10/2008 | Puckett | |
| 7,617,714 B2 | 11/2009 | Engelbart et al. | |
| 7,617,715 B2 | 11/2009 | Georgeson et al. | |
| 2004/0059010 A1* | 3/2004 | Nutt et al. ........................ | 521/56 |
| 2006/0280927 A1 | 12/2006 | Albright et al. | |
| 2007/0095141 A1* | 5/2007 | Puckett ........................... | 73/649 |
| 2010/0029796 A1* | 2/2010 | Alderson et al. ............... | 521/143 |
| 2010/0134098 A1 | 6/2010 | Faidi et al. | |
| 2011/0135872 A1 | 6/2011 | May et al. | |

FOREIGN PATENT DOCUMENTS

| | | |
|---|---|---|
| DE | 10129372 | 1/2003 |
| GB | 2221991 | 2/1990 |
| WO | 2008070705 | 6/2007 |
| WO | WO 2010/066692 A2 * | 6/2010 |
| WO | 2010148439 | 12/2010 |

OTHER PUBLICATIONS

EP search report for EP12176253 dated Feb. 6, 2013.

* cited by examiner

*Primary Examiner* — David Sample
*Assistant Examiner* — Nicole T Gugliotta

(57) ABSTRACT

A porous composite substrate that includes reinforcement material disposed within a resin matrix. The resin matrix includes a first matrix region with a first density, and a second matrix region with a second density that is different than the first density. The first matrix region includes a plurality of pores that are formed by pore forming material.

16 Claims, 3 Drawing Sheets

COMPOSITE SUBSTRATES WITH PREDETERMINED POROSITIES

This invention was made with government support under Contract No. N00019-Q2-C-2003 awarded by the United States Navy. The government may have certain rights in the invention.

BACKGROUND OF THE INVENTION

1. Technical Field

The present invention relates to composite substrates and, in particular, to composite substrates with predetermined porosities that may be utilized, for example, within a porosity reference standard or during evaluation of defects in gas turbine engine components.

2. Background Information

Non-destructive investigation "NDI" may be performed on organic matrix composite components to inspect for defects such as delaminations and/or relatively high porosities (e.g., typically greater than 2%). The term "porosity" describes a ratio of a volume of pores or voids within a composite component to a volume of composite component material. Non-destructive investigation may be performed using non-destructive investigation "NDI" machines such as, for example, ultrasound machines and thermography machines.

NDI machines are typically calibrated utilizing a porosity reference standard that includes a plurality of test panels, each having a different porosity level and depth within the panel. A typical test panel may include a polytetrafluoroethylene or plastic inclusion that is inserted within a composite test panel body. The inclusion is designed to replicate a certain porosity level when the test panel is inspected by an NDI machine. Alternatively, a composite test panel body may include a plurality of drilled apertures that are similarly designed to replicate a certain porosity level when the test panel is inspected by an NDI machine. Such test panels, however, may be difficult to implement in practice, which may lead to delays in delivering high cost organic matrix composite components to customers.

SUMMARY OF THE DISCLOSURE

According to a first aspect of the invention, a porous composite substrate includes a resin matrix and reinforcement material. The resin matrix includes a first matrix region surrounded by a second matrix region. The first matrix region includes a plurality of pores formed by pore forming material, and a first density. The second matrix region includes a second density that is different than the first density. The reinforcement material is disposed within the second matrix region.

According to a second aspect of the invention, a porosity reference standard is provided for non-destructive inspection of a composite material. The reference standard includes a composite first test panel and a composite second test panel. Each test panel includes reinforcement material disposed within a resin matrix that includes a first matrix region and a second matrix region. The first matrix region includes a plurality of pores formed by pore forming material, and a first density. The second matrix region includes a second density that is different than the first density.

The foregoing features and the operation of the invention will become more apparent in light of the following description and the accompanying drawings.

DETAILED DESCRIPTION OF THE INVENTION

Figure 1:
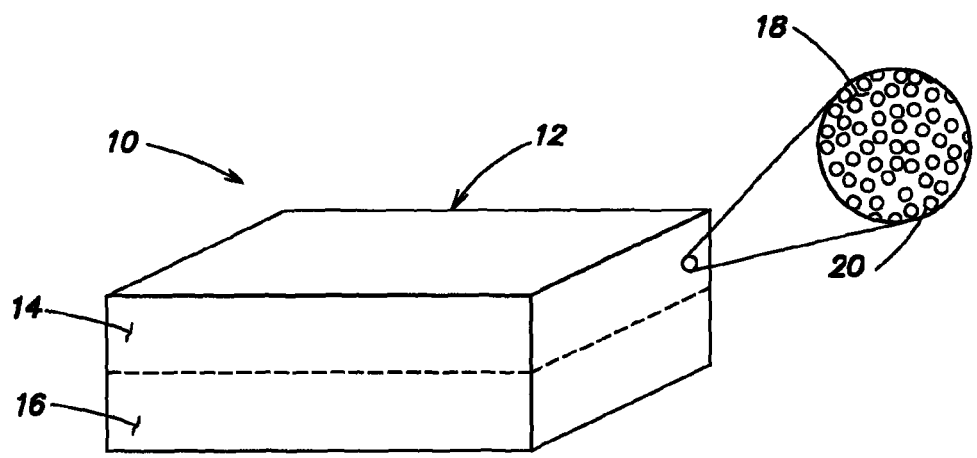
FIG. 1 is perspective illustration of a porous composite substrate, and an enlargement of a section of a first matrix region included in the composite substrate.

FIG. 1 is perspective illustration of a porous composite substrate 10 (e.g., an organic matrix composite "OMC" substrate). The composite substrate 10 includes a resin matrix 12 with a first matrix region 14 (e.g., a relatively porous matrix region with a porosity between about 0.1 and 25 percent) having a first density, and a second matrix region 16 (e.g., a relatively non-porous matrix region with a porosity between about zero and two percent) having a second density that may be different (e.g., greater) than the first density. The second density may be, for example, between about two to twenty five percent greater than the first density. The resin matrix 12 includes resin 18 and a plurality of pores 20.

Figure 2:
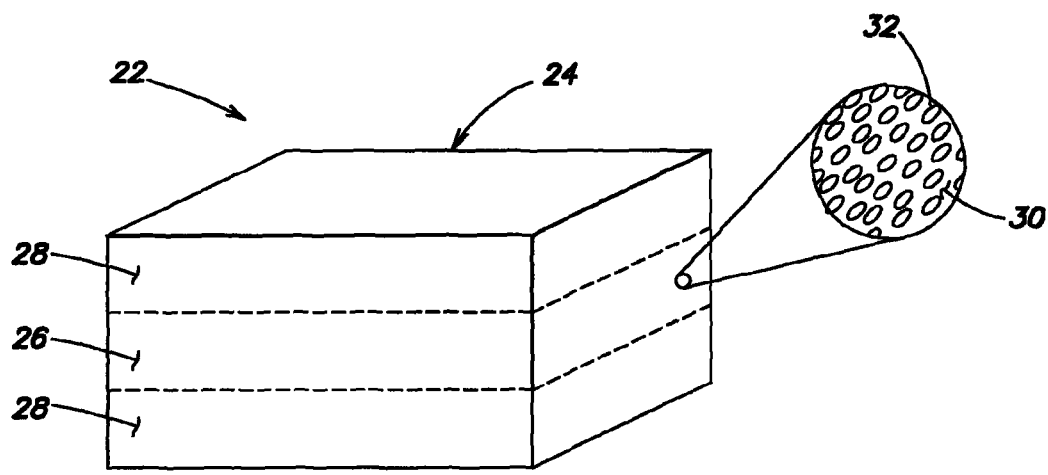
FIG. 2 is a perspective illustration of another porous composite substrate, and an enlargement of a section of a first matrix region included in the composite substrate.

FIG. 2 is a perspective illustration of another porous composite substrate 22. The composite substrate 22 includes a resin matrix 24 with a first matrix region 26 having a first density, and a plurality of second matrix regions 28 each having a second density that may be different (e.g., greater) than the first density. The first matrix region 26 is arranged between the second matrix regions 28. The resin matrix 24 includes resin 30 and a plurality of pores 32.

Referring to FIGS. 1 and 2, the type and/or components of the resin 18, 30 included in the resin matrix 12, 24 may be selected based on design parameters for each particular application of the substrate. Examples of suitable resins may include polyepoxides (e.g., thermosetting epoxies), maleimides (e.g., bismaleimide), and thermosetting or thermoplastic polyimides. Other examples of suitable resins may include polyesters, cyanate esters and benzoxazines. Other composite substrate embodiments, however, may include alternative resins that are selected based on the design parameters for each particular application of the substrate.

The pores 20, 32 may be distributed, for example, substantially uniformly throughout the first matrix region 14, 26, respectively. The pores may have, for example, circular cross-sectional or spherical geometries as illustrated in FIG. 1, and/or elongated (e.g., elliptical) cross-sectional geometries as illustrated in FIG. 2. The pores may be sized having overall dimensions (e.g., diameters for the circular geometries or major axis dimensions for the elongated geometries) between, for example, about 0.002 and 0.010 inches. Other composite substrate embodiments, however, may include pores having alternative cross-sectional geometries and/or sizes that are selected based on the design parameters for each particular application of the substrate.

The term "pore" is used herein to describe both an actual gas or vacuum filled cavity, and a solid material body that simulates a gas or vacuum filled cavity during non-destructive investigation "NDI" techniques such as, for example, ultrasound or thermography NDI techniques. The pores 20, 32 are formed, for example, with pore forming material that may include microballoon filler, microsphere filler and/or blowing agent (e.g., a thermally controlled, chemical blowing agent).

The microballoon filler includes a plurality of microballoons. Each microballoon includes a gas or vacuum filled cavity that forms a respective one of the pores (e.g., pores 20 in FIG. 1). The microballoons may be constructed from materials that are the same as or simulate, for example, the resin or other filler materials or reinforcement materials disposed within the resin matrix. Examples of suitable microballoon materials may include glass, phenolic resin, ceramic, carbon, thermosetting polymers and/or thermoplastic polymers. Other composite substrate embodiments, however, may include microballoons constructed from alternative materials that are selected based on the design parameters for each particular application of the substrate.

The microsphere filler includes a plurality of solid microspheres. The microspheres may be constructed from materials that simulate gas or vacuum filled cavities during non-destructive investigation techniques such as, for example, ultrasound or thermography NDI techniques. Examples of suitable microsphere materials may include glass, phenolic resin, ceramic, carbon, thermosetting polymers and/or thermoplastic polymers. Other composite substrate embodiments, however, may include microspheres constructed from alternative materials that are selected based on the design parameters for each particular application of the substrate.

The blowing agent includes a blowing agent material (e.g., chemical foaming agent) that decomposes, within the resin matrix, into gas that forms a plurality of gas filled cavities during manufacture of the composite substrate. Each gas filled cavity forms a respective one of the pores (e.g., pores 32 in FIG. 2). The blowing agent material may be selected to decompose over a relatively narrow temperature range (e.g., between about one to eighteen degrees Fahrenheit) that occurs, for example, just prior to gelation or vitrification of the resin. The blowing agent material may include, for example, benzenesulfonyl hydrazide to form pores within a bismaleimide based resin matrix. Other examples of suitable blowing agents may include azodicarboamides and p,p'-oxybis (sulfonylhydrazide). Other composite substrate embodiments, however, may include alternative blowing agent materials that are selected based on the design parameters for each particular application of the substrate.

Referring still to FIGS. 1 and 2, the composite substrate 10, 22 may also include reinforcement material disposed within the first matrix region 14, 26 and/or the second matrix region(s) 16, 28. The reinforcement material may include a plurality of reinforcement material fibers that are, for example, woven into a sheet or arranged into a unidirectional tape. Alternatively, the reinforcement material may include a plurality of reinforcement material filler particles. Examples of suitable reinforcement materials may include carbon, aramid, fiberglass, glass and/or ceramic. Other composite substrate embodiments, however, may include alternative reinforcement materials that are selected based on the design parameters for each particular application of the substrate.

The composite substrates 10, 22 may be manufactured utilizing composite molding methods such as autoclave molding, compression molding, resin transfer molding, etc. During manufacture of the composite substrate 10 illustrated in FIG. 1, for example, a first woven sheet of fiber reinforced material is fully or partially preimpregnated with, for example, a substantially homogeneous mixture of resin and microballoon filler. The resin within the first woven sheet is subsequently partially cured to provide a relatively porous first layer of prepreg fiber reinforced material; e.g., a layer with a porosity between about one tenth and ten percent. A second woven sheet of fiber reinforced material is also fully or partially preimpregnated with the resin, and subsequently partially cured to provide a relatively non-porous second layer of prepreg fiber reinforced material; e.g., a layer with a porosity less than about zero to two percent. The first layer is stacked on the second layer, and the stack may be placed into an autoclave. The stack is heated, which bonds the first layer and the second layer together into the composite substrate 10. The first layer forms the first matrix region 14, and the second layer forms the second matrix region 16.

In another example, during the manufacture of the composite substrate 22 illustrated in FIG. 2, a substantially homogeneous mixture of resin and blowing agent is processed into an uncured resin film. One or more sheets of reinforcement material are fully or partially preimpregnated with resin to provide a first set of prepreg sheets. One or more additional sheets of reinforcement material are fully or partially preimpregnated with resin to provide a second set of prepreg sheets. The uncured resin film is arranged between the first set of prepreg sheets and the second set of prepreg sheets to provide a stack. The stack is subsequently heated and compressed such that the uncured resin film migrates into the prepreg sheets within the first matrix region 26. Prior to (e.g., just prior to) gelation or vitrification of the resin, the blowing agent decomposes and creates a plurality of gas filled cavities that form the pores 32 in the first matrix region 26.

Figure 3:
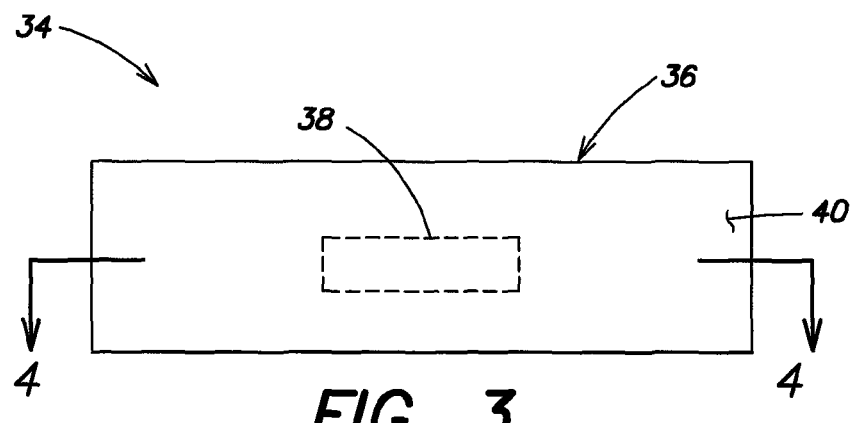
FIG. 3 is a sectional illustration of another porous composite substrate.
Figure 4:
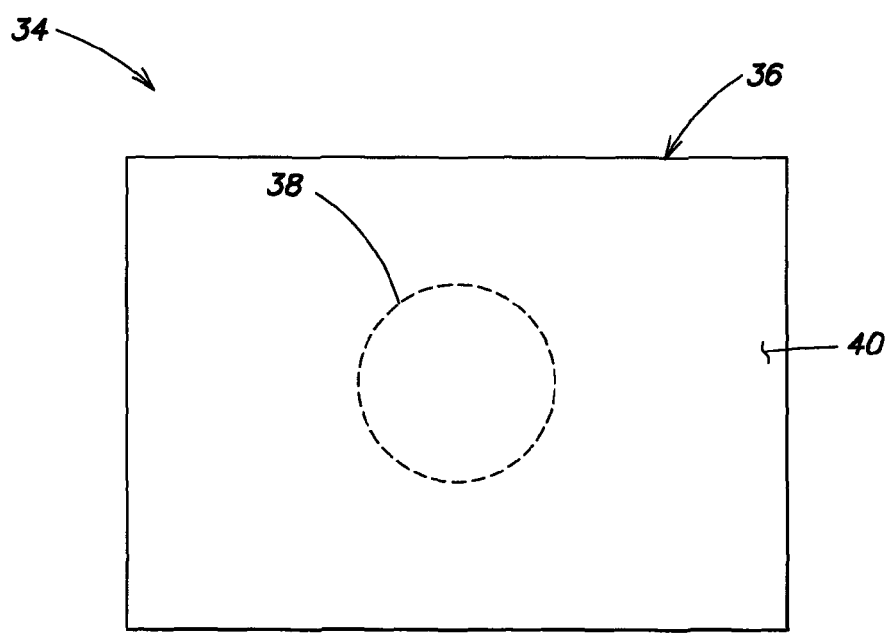
FIG. 4 is a cross-sectional illustration of the composite substrate illustrated in FIG. 3.

FIG. 3 is a sectional illustration of another porous composite substrate 34. FIG. 4 is a cross-sectional illustration of the composite substrate 34. The composite substrate 34 includes fibrous reinforcement material disposed within a resin matrix 36 (e.g., CYCOM® 5250-4 resin manufactured by Cytec, which is located in Woodland Park, N.J.). The resin matrix 36 has a first matrix region 38 (e.g., a relatively porous matrix region with a porosity between about 0.1 and 10 percent) that is surrounded on each side by (e.g., embedded within) a second matrix region 40 (e.g., a relatively non-porous matrix region with about zero porosity). The first matrix region 38 has a first density (e.g., between about 1.23 and 1.25 grams per cubic centimeter (g/cc) for a bismaleimide based matrix). The second matrix region 40 has a second density (e.g., between about 1.12 and 1.25 g/cc for the bismaleimide based matrix) that may be different (e.g., greater) than the first density. The resin matrix 36 includes resin and a plurality of pores disposed throughout the first matrix region 38.

The composite substrate 34 may be manufactured utilizing composite molding methods such as autoclave molding, compression molding, resin transfer molding, liquid molding, etc. For example, the first matrix region 38 may be created by cutting an uncured resin film of resin and blowing agent into a circular disk. The cut resin film is disposed between, for example, two sets of preimpregnated sheets of reinforcement material to provide a stack. The stack may be compressed and heated such that the cut resin film migrates into portions of the preimpregnated sheets within the first matrix region 38, and the blowing agent decomposes and forms the pores.

Figure 5:
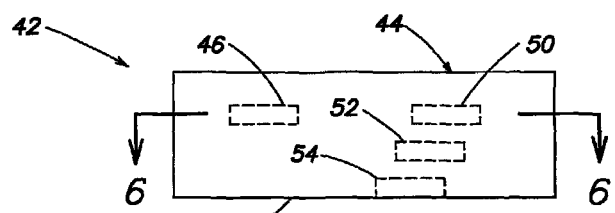
FIG. 5 is a sectional illustration of another porous composite substrate.
Figure 6:
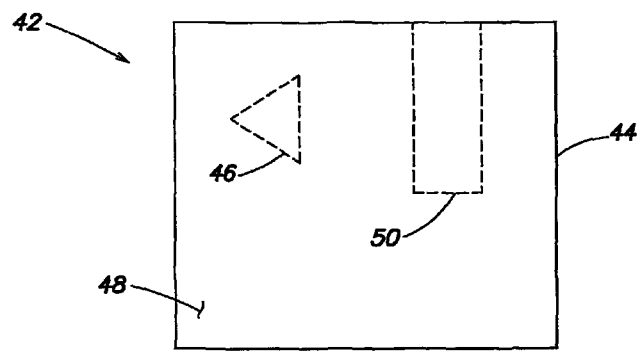
FIG. 6 is a cross-sectional illustration of the composite substrate illustrated in FIG. 5.

FIG. 5 is a sectional illustration of another porous composite substrate 42. FIG. 6 is a cross-sectional illustration of the composite substrate 42. The composite substrate 42 includes fibrous reinforcement material disposed within a resin matrix 44. The resin matrix 44 has a first matrix region 46 that is surrounded on each side by (e.g., encased within) a second matrix region 48. The composite substrate 42 may also have a third matrix region 50, a fourth matrix region 52 and a fifth matrix region 54, which are partially surrounded by the second matrix region 48. The first matrix region 46 has a first density. The second matrix region 48 has a second density that may be different (e.g., greater) than the first density. Each of the third, fourth and fifth matrix regions 50, 52, 54 also have a respective density that may be different (e.g., less) than the second density. The densities of the third, fourth and fifth matrix regions may also be different than the first density. The resin matrix 44 includes resin, and a plurality of pores disposed throughout the first, third, fourth and fifth matrix regions 46, 50, 52 and 54.

The composite substrate 42 may be manufactured utilizing composite molding methods such as autoclave molding, compression molding, resin transfer molding, liquid molding, etc. For example, the first, third, fourth and fifth matrix regions 46, 50, 52 and 54 may be created by preimpregnating respective sheets of fiber reinforced material with, for example, a substantially homogeneous mixture of resin and microballoon filler. The resin in the preimpregnated sheets may be partially cured to provide relatively porous insert layers of preimpregnated fiber reinforce material. Each insert layer may be cut into a desired shape, and respectively arranged between relatively non-porous core layers of preimpregnated fiber reinforced material to provide a stack. The stack may be compressed and heated to create the composite substrate.

The composite substrates 10, 22, 34 and 42 illustrated in FIGS. 1-5 may be used for a variety of different applications. A porosity reference standard for non-destructive inspection of a composite material, for example, may include a plurality of composite test panels respectively molded from a plurality of porous composite substrates according to the present invention. Each of the composite substrates (e.g., test panels) in the reference standard may be constructed having a first matrix region with a different determinable porosity. The porosity of each composite substrate may be determined, for example, during manufacture based on the quantity of the pore forming material added to the resin. A total volume of the microballoon cavities can be calculated, for example, based on the quantity of the microballoon filler added to the resin. Similarly, a total volume of gas filled cavities that are created within the first matrix region by a blowing agent may be calculated based on the quantity of the blowing agent added to the resin, and the blowing agent decomposition characteristics.

In some embodiments, each test panel may include a plurality of different defect levels; e.g., where each test panel includes a plurality of the second matrix regions.

Figure 7:
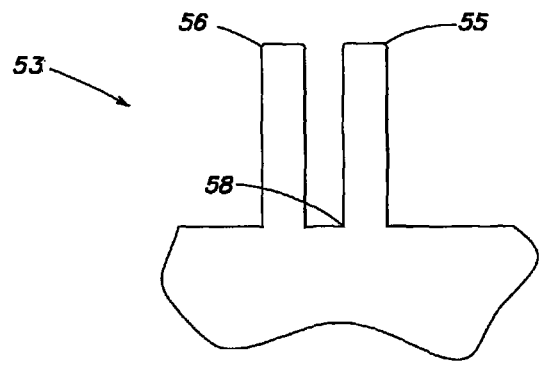
FIG. 7 is a partial sectional illustration of a gas turbine engine component.

In another example, a porous composite substrate according to the present invention may be molded into at least a portion of a gas turbine engine component (e.g., a shaft, a rotor blade, a stator vane, etc.). FIG. 7 is a partial sectional illustration of a gas turbine engine component 53 that includes one or more flanges 55 and 56. The composite substrate may be molded such that its first matrix region is located, for example, at a corner 58 of the flange 55. Various durability and stress tests may be performed on the component 53 and the flange 55 to determine how such a gas turbine engine component with a porous region (e.g., greater than 2%) will perform during engine operation. Such a technique may be used, for example, where NDI techniques are difficult to perform.

While various embodiments of the present invention have been disclosed, it will be apparent to those of ordinary skill in the art that many more embodiments and implementations are possible within the scope of the invention. Accordingly, the present invention is not to be restricted except in light of the attached claims and their equivalents.

What is claimed is:

1. A porous composite substrate, comprising:
a resin matrix comprising a first matrix region surrounded by a second matrix region, wherein the first matrix region comprises a plurality of pores and a first density, wherein the second matrix region comprises a second density that is different than the first density, and wherein the pores are formed by pore forming material; and
reinforcement material disposed within the second matrix region, the reinforcement material comprising a plurality of core layers of fiber reinforced material;
wherein the first matrix region comprises an insert layer of fiber reinforced material that is disposed within the second matrix region and between adjacent core layers.

2. The composite substrate of claim 1, wherein the pore forming material comprises at least one of a plurality of microballoons and a plurality of microspheres.

3. The composite substrate of claim 1, wherein the pore forming material comprises blowing agent that forms a plurality of gas filled cavities during substrate manufacture, and wherein a first one of the plurality of the gas filled cavities forms a respective one of the pores.

4. The composite substrate of claim 1, wherein a first one of the plurality of the pores comprises one of an elongated geometry and a spherical geometry.

5. The composite substrate of claim 1, wherein the resin matrix and the reinforcement material are formed into at least a portion of a gas turbine engine component.

6. The composite substrate of claim 5, wherein the second matrix region is arranged in one of a corner and a flange of the engine component.

7. The composite substrate of claim 5, wherein the engine component comprises one of a shaft, a rotor blade and a stator vane.

8. The composite substrate of claim 1, wherein the resin matrix further comprises a third matrix region that comprises a plurality of second pores and a third density that is different than the second density.

9. The composite substrate of claim 1, wherein the pores are substantially uniformly distributed within the first matrix region.

10. A porosity reference standard for non-destructive inspection of a composite material, comprising a composite first test panel and a composite second test panel, each test panel comprising reinforcement material disposed within a resin matrix that comprises a first matrix region and a second matrix region, wherein the first matrix region comprises a plurality of pores and a first density, wherein the second matrix region comprises a second density that is different than the first density, and wherein the pores are formed by pore forming material, wherein the reinforcement material in the first test panel comprises a plurality of core layers of fiber reinforced material, and wherein the first matrix region of the first test panel comprises an insert layer of fiber reinforced material that is disposed within the second matrix region and between adjacent core layers.

11. The porosity reference standard of claim 10, wherein the first matrix region in the first test panel comprises a first porosity, and wherein the first matrix region in the second test panel comprises a second porosity that is different than the first porosity.

12. The porosity reference standard of claim 10, wherein the pore forming material comprises at least one of a plurality of microballoons and a plurality of microspheres.

13. The porosity reference standard of claim 10, wherein the pore forming material comprises blowing agent that forms a plurality of gas filled cavities during test panel manufacture, and wherein a first one of the plurality of the gas filled cavities forms a respective one of the pores.

14. The porosity reference standard of claim 10, wherein a first one of the plurality of the pores in the first test panel comprises one of an elongated geometry and a spherical geometry.

15. The porosity reference standard of claim 10, wherein the first matrix region in the first test panel is surrounded by the second matrix region.

16. The porosity reference standard of claim 10, wherein the resin matrix in the first test panel further comprises a third matrix region that comprises a plurality of second pores and a third density that is different than the second density.

* * * * *